United States Patent
Choi et al.

(10) Patent No.: US 9,668,815 B2
(45) Date of Patent: Jun. 6, 2017

(54) SURGICAL ROBOT

(71) Applicant: Samsung Electronics Co., Ltd., Suwon-si (KR)

(72) Inventors: Byung June Choi, Gunpo-si (KR); Young Bo Shim, Seoul (KR); Yong Jae Kim, Seoul (KR); Jeong Hun Kim, Hwaseong-si (KR); Se Gon Roh, Suwon-si (KR); Youn Baek Lee, Suwon-si (KR); Jong Won Lee, Uiwang (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 686 days.

(21) Appl. No.: 14/035,155

(22) Filed: Sep. 24, 2013

(65) Prior Publication Data
US 2014/0303644 A1    Oct. 9, 2014

(30) Foreign Application Priority Data

Apr. 8, 2013  (KR) ........................ 10-2013-0037939

(51) Int. Cl.
*A61B 34/30*  (2016.01)
*A61B 19/00*  (2006.01)
*A61B 34/37*  (2016.01)

(52) U.S. Cl.
CPC .......... *A61B 19/2203* (2013.01); *A61B 34/30* (2016.02); *A61B 34/37* (2016.02); *A61B 2034/306* (2016.02)

(58) Field of Classification Search
CPC ........ A61B 19/2203; A61B 2019/2223; A61B 2017/00314; A61B 2017/00398
See application file for complete search history.

(56) References Cited

U.S. PATENT DOCUMENTS

2006/0155160 A1*  7/2006  Melvin ............ A61B 17/00234
                                                                    600/16
2010/0193566 A1*  8/2010  Scheib ............. A61B 17/07207
                                                                    227/175.2

FOREIGN PATENT DOCUMENTS

JP      2012-516753      7/2012
KR      10-2010-0138898  12/2010
KR      10-2012-0036158  4/2012

* cited by examiner

*Primary Examiner* — Katherine M Shi
*Assistant Examiner* — Michael Mendoza
(74) *Attorney, Agent, or Firm* — Harness, Dickey & Pierce, P.L.C.

(57) ABSTRACT

A surgical robot including a slave device provided with a surgical instrument includes a body having at least one link that includes a plurality of solenoid segments, and an end effector mounted to one end of the body.

21 Claims, 8 Drawing Sheets

SURGICAL ROBOT

CROSS-REFERENCE TO RELATED APPLICATIONS

This application claims the priority benefit of Korean Patent Application No. 10-2013-0037939, filed on Apr. 8, 2013 in the Korean Intellectual Property Office, the disclosure of which is incorporated herein by reference.

BACKGROUND

1. Field

The following description relates to a surgical robot including a surgical instrument that may be switched between a bendable state and a rigid state.

2. Description of the Related Art

Minimally invasive surgery refers to surgical methods to minimize the size of an incision. Laparotomy uses a relatively large surgical incision through a part of a human body (e.g., the abdomen). However, in minimally invasive surgery, after forming at least one small port (or incision) of 0.5 cm~1.5 cm through the abdominal wall, an operator inserts an endoscope and a variety of surgical instruments through the port, to perform surgery while viewing an image.

Compared to laparotomy, minimally invasive surgery has several advantages, such as low pain after surgery, early recovery, early restoration of ability to eat, short hospitalization, rapid return to daily life, and superior cosmetic effects due to a small incision. Accordingly, minimally invasive surgery has been used in gall resection, prostate cancer, and herniotomy operations, etc, and the use range thereof continues to expand.

In general, a surgical robot used in minimally invasive surgery includes a master device and a slave device. The master device generates a control signal corresponding to doctor manipulation to transmit the control signal to the slave device. The slave device receives the control signal from the master device to perform manipulation required for surgery of a patient. The master device and the slave device may be integrated with each other, or may be separately arranged in an operating room.

Examples of surgical robots include a multi-port surgical robot that forms a plurality of incisions in the body of a patient to insert a plurality of surgical instruments through the respective incisions in a one-to-one ratio, and a single-port surgical robot that forms a single incision in the body of the patient to insert a plurality of surgical instruments through the single incision at once. Here, the single-port surgical robot forms a single incision differently from the multi-port surgical robot and has been given more attention due to advantages of the narrow incision and early recovery. However, single-port surgery is not easy.

SUMMARY

It is an aspect of the present disclosure to provide a surgical robot including a surgical instrument configured to easily pass through a bent guide tube.

Additional aspects of the disclosure will be set forth in part in the description which follows and, in part, will be obvious from the description, or may be learned by practice of the invention.

In accordance with an aspect of the disclosure, in a surgical robot including a slave device provided with a surgical instrument, the surgical instrument includes a body having at least one link that includes a plurality of solenoid segments, and an end effector mounted to one end of the body.

In accordance with an aspect of the disclosure, a surgical robot includes a body including a plurality of electromagnetic solenoid segments, where at least a portion of the body becomes rigid or flexible depending on a generated polarity of an energized state of each of the plurality of electromagnetic solenoid segments.

In accordance with an aspect of the disclosure, a method of controlling a surgical robot including a body including a plurality of electromagnetic solenoid segments includes energizing a first portion of the electromagnetic solenoid segments with a first voltage, and energizing a second portion of the electromagnetic solenoid segments with a second voltage, where the plurality of electromagnetic solenoid segments are selectively rigid or flexible depending on the first voltage and the second voltage.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
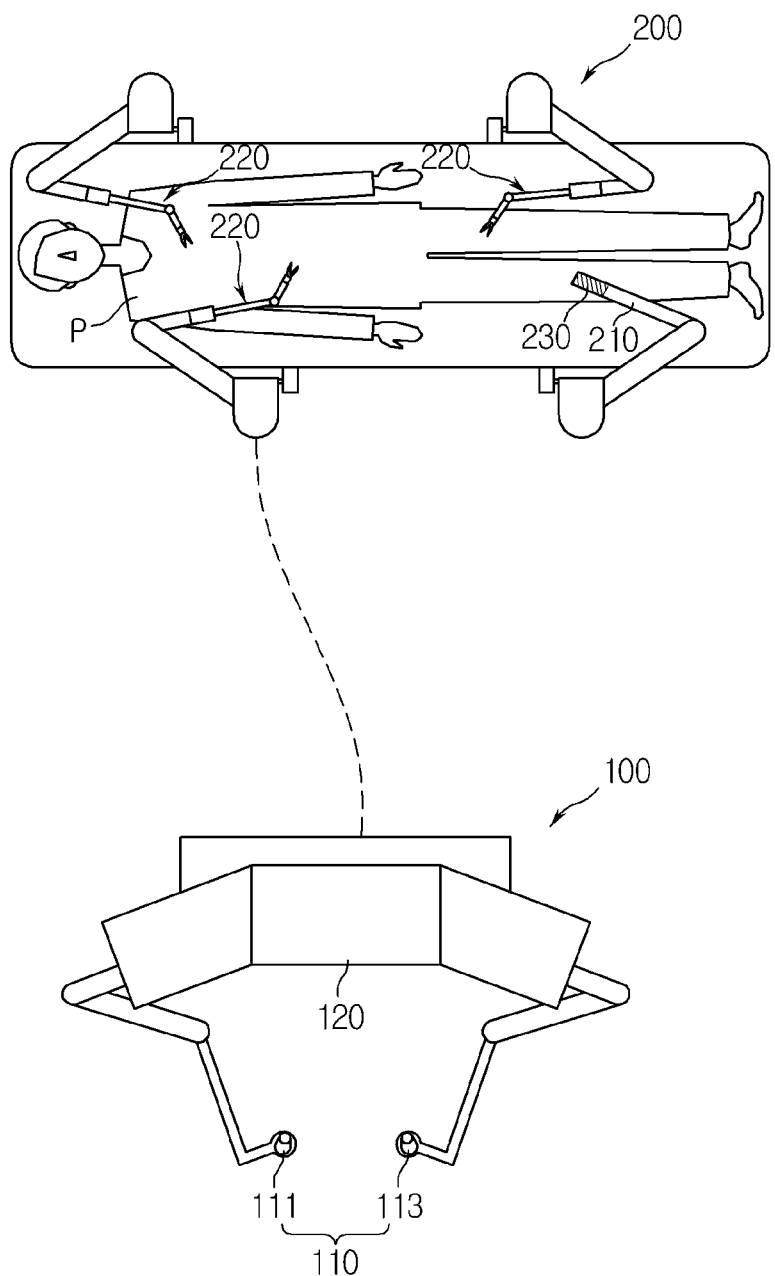
FIG. 1 is a view showing an outer appearance of a surgical robot.

Aspects, specific advantages and novel features of the embodiments of the present disclosure will become apparent with reference to the following detailed description and embodiments described below in detail in conjunction with the accompanying drawings. It is noted that the same or similar elements are denoted by the same reference numerals even though they are depicted in different drawings. In addition, a detailed description of well-known techniques may be omitted to avoid unnecessarily obscuring the present disclosure. Herein, the terms first, second, etc. are used simply to discriminate any one element from other elements, and the elements are not limited to these terms.

Hereinafter, reference will now be made in detail to the embodiments of the present disclosure, examples of which are illustrated in the accompanying drawings, wherein like reference numerals refer to like elements throughout.

The disclosure may be applied to a single-port surgical robot, without being in any way limited thereto. The single-port surgical robot is configured to perform surgery by inserting a plurality of surgical instruments into the abdominal cavity of the patient through a single incision. The single-port surgical robot may be different from a multi-port surgical robot that forms a plurality of incisions and inserts one surgical instrument through each incision.

In addition, although a surgical robot including a slave device and a master device to remotely control the slave device will be described hereinafter by way of example, the disclosure may naturally be applied to a surgical robot that permits an operator to directly manipulate a surgical instrument.

Figure 2:
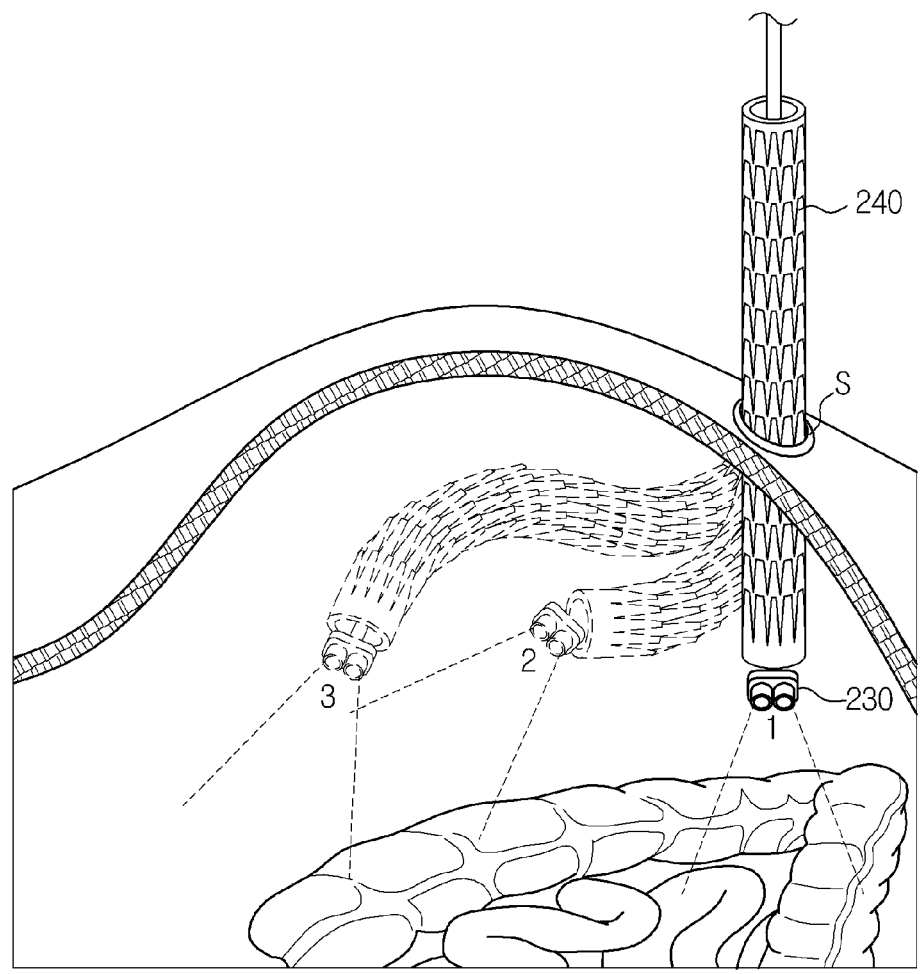
FIG. 2 is a view showing a state in which a guide tube for insertion of a surgical instrument is inserted into the abdominal cavity and moved to a surgical region.
Figure 3:
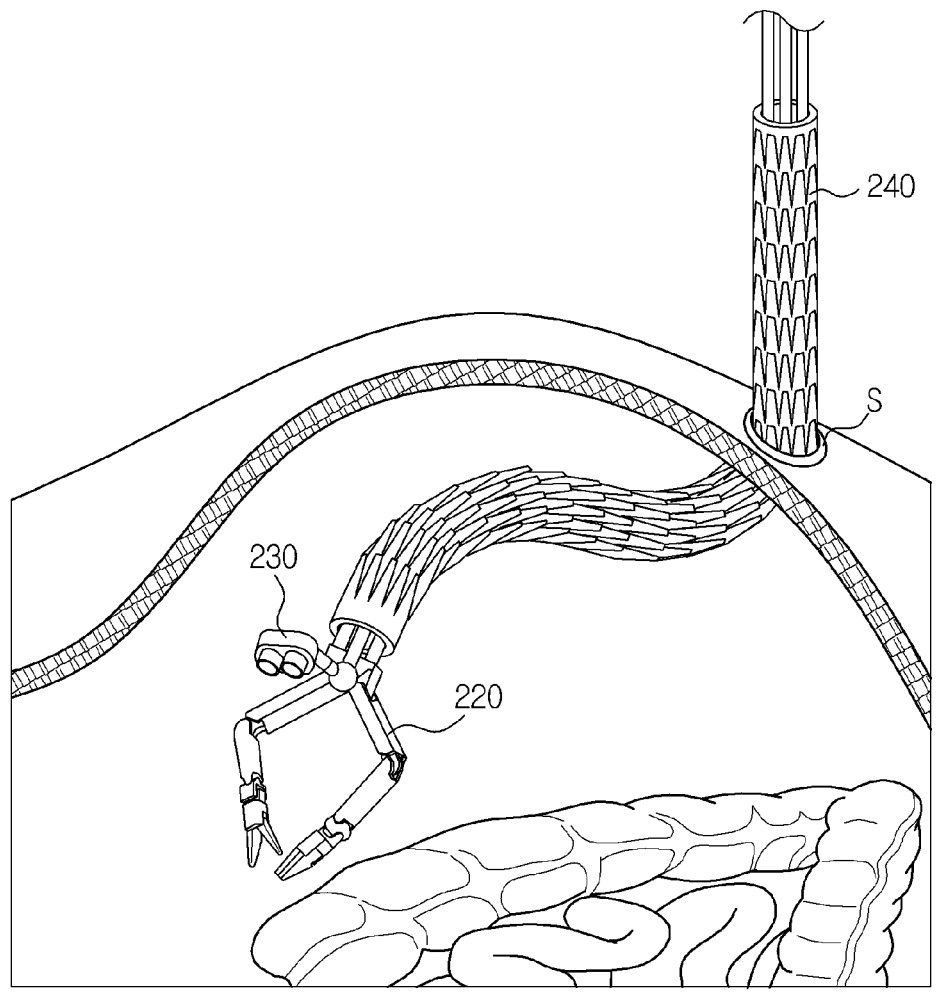
FIG. 3 is a view showing a state in which a surgical instrument is inserted into the guide tube that has been moved to the surgical region.

FIG. 1 is a view showing an outer appearance of a surgical robot, FIG. 2 is a view showing a state in which a guide tube for insertion of a surgical instrument is inserted into the abdominal cavity and moved to a surgical region, and FIG. 3 is a view showing a state in which a surgical instrument is inserted into the guide tube that has been moved to the surgical region.

Referring to FIG. 1, the surgical robot may include a slave device 200 to perform surgery on a patient P who lies on an operating table, and a master device 100 to assist an operator (e.g., a doctor) in remotely controlling the slave device 200. In this case, at least one assistant (not shown) who assists the operator (not shown) may be located near the patient P.

Here, assisting the operator may refer to assisting remote surgery by the operator in a space where the patient P is located. This assistance may include a change of used surgical instruments, without being in any way limited thereto. For example, various surgical instruments may be used according to the kind of surgery and the number of robot arms 210 of the slave device 200, and consequently, the number of surgical instruments used at once may be limited. In addition, because there is a single incision, the number of surgical instruments to be inserted into the abdominal cavity of the patient P may be limited.

Accordingly, to change surgical instruments during surgery, the operator may instruct an assistant near the patient P to change surgical instruments, and the assistant may change surgical instruments according to the operator's instruction by pulling out the surgical instruments inserted in the abdominal cavity of the patient P and inserting other surgical instruments, or by separating the surgical instruments mounted to the robot arms 210 and reinstalling other surgical instruments to the robot arms 210.

The master device 100 and the slave device 200 may be physically separate devices, without being in any way limited thereto. Also, the master device 100 and the slave device 200 may be integrated with each other.

As exemplarily shown in FIG. 1, the master device 100 may include an input unit 110 and a display unit 120.

The input unit 110 may receive an instruction input by the operator, such as an instruction for selection of an operation mode of the surgical robot, or an instruction for remote control of motion of robot arms 210, surgical instruments 220, and an image capture unit 230 of the slave device 200, for example. The input unit 110 according to the present embodiment may include a haptic device, clutch pedal, switch, button, or the like, without being in any way limited thereto. As an example, a voice recognition device may be used. It will be clearly understood that the haptic device will be described hereinafter as an example of the input unit 110, but the aforementioned various other devices may be used as the input unit 110.

Although FIG. 1 shows the input unit 110 with two handles 111 and 113, the disclosure is not limited thereto. For example, the input unit 110 may include one handle, or three or more handles. The operator may control motion of the robot arms 210 of the slave device 200 by moving the two handles 111 and 113 with both hands. That is, if the operator manipulates the input unit 110, a controller (not shown) may generate a control signal corresponding to information regarding the state of the input unit 110, and may transmit the control signal to the slave device 200 via a communication unit (not shown). Here, the control signal may include an instruction to control motions of the robot arms 210, the surgical instruments 220, and the image capture unit 230, as described above, without being in any way limited thereto.

The display unit 120 of the master device 100 may display, e.g., an image of the interior of the patient's body collected via the image capture unit 230 and a 3D virtual image generated using medical images of the patient before surgery. To this end, the master device 100 may include an image processor (not shown) that receives and processes image data transmitted from the slave device 200 to output the processed data to the display unit 120. Here, the image data may include a 3D virtual image generated using medical images of the patient before surgery as well as an image collected via the image capture unit 230, without being in any way limited thereto.

The display unit 120 may include one or more monitors such that the respective monitors individually display information required for surgery. For example, if the display unit 120 includes three monitors, one of the monitors may display an image collected via the image capture unit 230, and the other two monitors may respectively display a 3D image generated using medical images of the patient before surgery, and information regarding motion of the slave device 200, as well as patient information. As an example, a plurality of monitors may display the same image. In this case, the respective monitors may display the same image, or a single image may be displayed on all of the plurality of monitors. In addition, the number of monitors may be determined in various ways according to the type or kind of information to be displayed. The aforementioned display unit 120, for example, may be a Liquid Crystal Display (LCD) unit or a Light Emitting Diode (LED) unit, for example, without being in any way limited thereto.

Here, patient information may refer to information regarding the state of the patient, for example, patient vital signs, such as body-temperature, pulse, respiration-rate, blood-pressure, etc. To provide the master device 100 with the vital signs, the slave device 200 that will be described hereinafter may further include a vital sign measurement unit including a body-temperature measurement module, a pulse measurement module, a respiration-rate measurement module, a blood-pressure measurement module, etc. To this end, the master device 100 may further include a signal processor (not shown) that receives and processes information transmitted from the slave device 200 to output the processed information to the display unit 120.

The slave device 200 may include a plurality of robot arms 210, and surgical instruments 220 mounted at ends of the respective robot arms 210.

Although not shown in detail in FIG. 1, each of the plurality of robot arms 210 may include a plurality of links and a plurality of joints. Each joint may serve to connect two links to each other, and may have 1 degree of freedom (DOF) or more. The DOF refers to a DOF with regard to kinematics or inverse kinematics. The DOF of a mechanism refers to the number of independent motions of the mechanism, or the number of variables that determine independent motions at relative positions between links. For example, an object in a 3D space defined by X-, Y-, and Z-axes has 3 DOF to determine a spatial position of the object (a position on each axis) and/or 3 DOF to determine a spatial orientation of the object (a rotation angle relative to each axis). More specifically, it will be appreciated that an object has 6 DOF if the object is movable along each of X-, Y-, and Z-axes and is rotatable about each of X-, Y-, and Z-axes.

Each joint of the robot arm 210 may be provided with a detector (not shown) to detect information regarding the state of each joint. For example, the detector (not shown) may include a force/torque detector to detect information regarding force/torque applied to the joint, a position detector to detect information regarding a position of the joint, and a speed detector to detect information regarding a movement speed of the joint. Here, the speed detector may be omitted according to the kind of position sensor that is used as the position detector. In this case, the position sensor may be a potentiometer or an encoder, for example, without being in any way limited thereto. As the detector is provided at each joint of the robot arm 210, a position and direction of the surgical instrument 220 may be calculated by detecting information regarding the state of each joint via the detector and subjecting the detected information to inverse kinematics.

In addition, in the present embodiment, all of the surgical instruments 220 may be inserted through a single incision, i.e. a single port formed in the abdomen of the patient P, without being in any way limited thereto. Such single-port surgery in which all of the surgical instruments 220 are inserted into a single port S formed in the abdomen of the patient P may advantageously minimize scarring and ensure early recovery as compared to multi-port surgery in which a plurality of incisions is formed in the abdomen of the patient P and a single surgical instrument is inserted through each incision.

In the present embodiment, the surgical instruments 220 may reach a surgical region by passing through a passage (not shown) defined in a guide tube 240 that is inserted into the single port S and is bendable to face the surgical region as exemplarily shown in FIG. 3. For example, as exemplarily shown in FIG. 2, after the guide tube 240, to which the image capture unit 230 has been mounted, is introduced into the single port S formed in the abdomen of the patient P, the guide tube 240 is moved to a surgical region (illustrated by being moved from position 1 to position 2 to position 3), and the image capture unit 230 mounted to the guide tube 240 captures an image inside the abdomen. After movement of the guide tube 240 is completed, as exemplarily shown in FIG. 3, a variety of surgical instruments 220 may reach the surgical region by passing through a surgical instrument introduction passage (not shown) defined in the guide tube 240.

In this case, because the guide tube 240 is bent, the surgical instrument introduction passage (not shown) defined in the guide tube 240 is also bent. Therefore, the surgical instrument 220 may need to be flexible to bend while passing through the bent surgical instrument introduction passage (not shown) of the guide tube 240, and may need to be rigid during surgery after having passed through the guide tube 240 for manipulation convenience and safety. That is, in the present embodiment, the surgical instrument 220 may be controlled to be in a bendable state or a rigid state according to situations.

Figure 4:
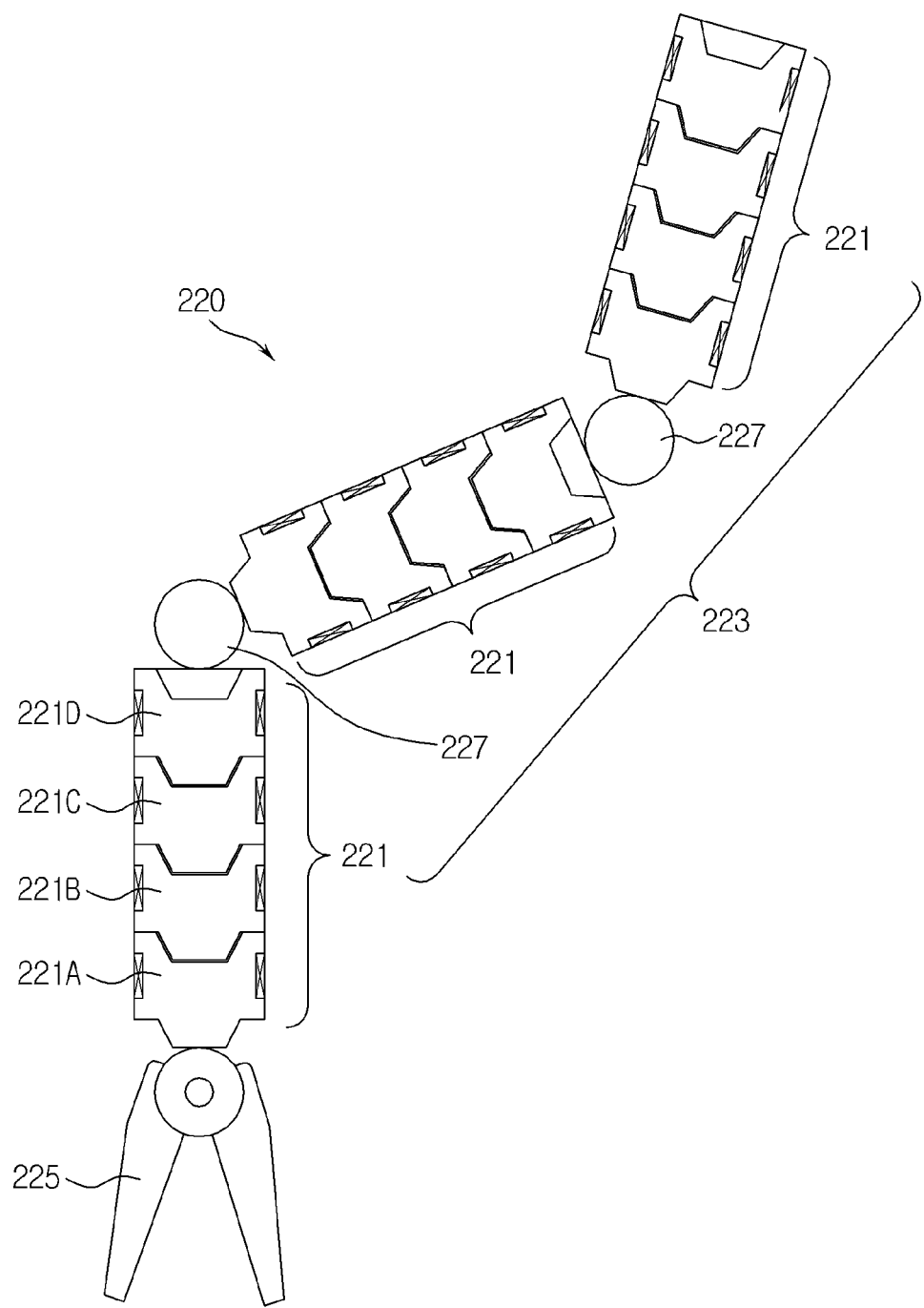
FIG. 4 is a view showing a configuration of the surgical instrument.

To this end, the surgical instrument 220 according to the present embodiment, as exemplarily shown in FIG. 4, may include a body 223 having at least one link 221 that is comprised of a plurality of solenoid segments 221A, 221B, 221C, and 221D and an end effector 225 mounted to one end of the body 223. Here, the solenoid segment may refer to a minimal unit component that includes an electromagnet that operates when current passes therethrough. Each of the solenoid segments 221A, 221B, 221C, and 221D may contain coils (510 and 520, see FIG. 5) to generate a magnetic field according to current passing therethrough. In this case, the coils 510 and 520 may include a first coil 510 to which first power is applied and a second coil 520 to which second power is applied as will be described hereinafter. In addition, as exemplarily shown in FIG. 5, each of the solenoid segments 221A, 221B, 221C, and 221D may have first holes 222A for passage of the first coils 510 and second holes 222B for passage of the second coils 520.

The respective solenoid segments 221A, 221B, 221C, and 221D may take the form of a hollow cylinder that defines a central passage, without being in any way limited to this shape, and the solenoid segments may have various other shapes. In this case, a variety of wires having different functions may pass through the central passages of the solenoid segments 221A, 221B, 221C, and 221D. Here, the variety of wires may include, for example, a wire to transmit drive power to the end effector 225 and a wire to enhance coupling strength when the solenoid segments 221A, 221B, 221C, and 221D are coupled to each other via generation of an attractive force, without being in any way limited thereto. This will hereinafter be described in detail.

Although FIG. 4 shows the link 221 as including the four solenoid segments 221A, 221B, 221C, and 221D, the number of the solenoid segments constituting one link 221 is not in any way limited.

In addition, in the present embodiment, the plurality of solenoid segments 221A, 221B, 221C, and 221D may be arranged in a line as exemplarily shown in FIG. 4. On the basis of a first solenoid segment 221A among the solenoid segments 221A, 221B, 221C, and 221D arranged in a line, first power may be applied to odd-numbered solenoid segments 221A and 221C and second power may be applied to even-numbered solenoid segments 221B and 221D.

That is, the odd-numbered solenoid segments 221A and 221C are connected to the first coils 510 to which first power is applied and the even-numbered solenoid segments 221B and 221D are connected to the second coils 520 to which second power is applied. As such, if first power and second power are applied respectively to the first coils 510 and the second coils 520, the odd-numbered solenoid segments 221A and 221C may simultaneously act as electromagnets having the same polarity, and the even-numbered solenoid segments 221B and 221D may simultaneously act as electromagnets having the same polarity.

The odd-numbered solenoid segments 221A and 221C and the even-numbered solenoid segments 221B and 221D are respectively connected and coupled to the first coils 510 and the second coils 520. In such a coupled state, as a current flow direction of first power and second power applied to the first coils 510 and the second coils 520 is changed, repulsive force or attractive force may be generated between the odd-numbered solenoid segments 221A and 221C and the even-numbered solenoid segments 221B and 221D. A detailed description thereof is as follows.

Figure 5:
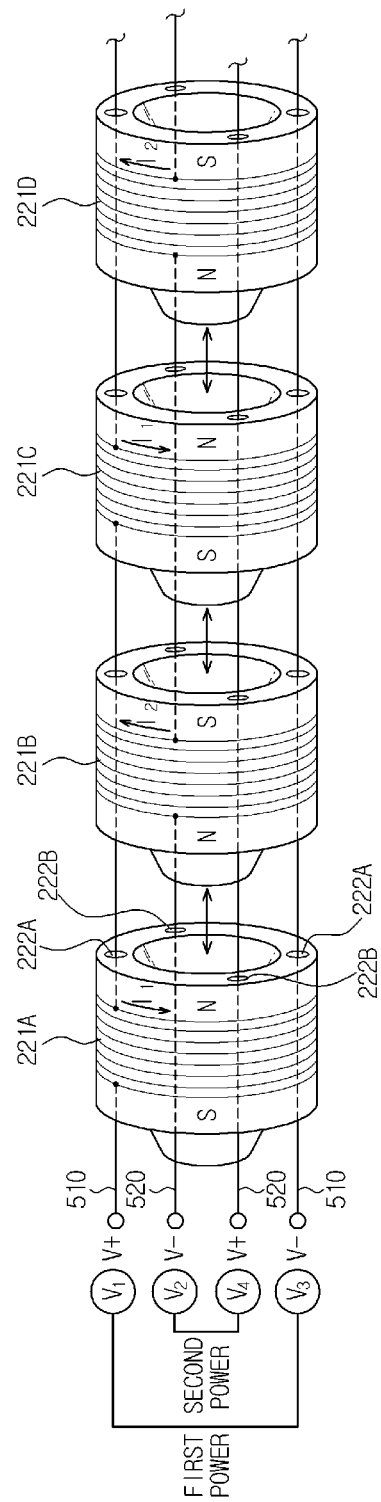
FIG. 5 is a view showing generation of repulsive force between respective segments constituting a link of the surgical instrument of FIG. 4.

First, referring to FIG. 5, all of the odd-numbered solenoid segments 221A and 221C are connected to the first coils 510 to which first power is applied, and all of the even-numbered solenoid segments 221B and 221D are connected to the second coils 520 to which second power is applied. In this case, terminals for application of first power are represented by $V_1$ and $V_3$, and terminals for application of second power are represented by $V_2$ and $V_4$. As exemplarily shown in FIG. 5, if (+) voltage and (−) voltage are respectively applied to the terminals $V_1$ and $V_3$ of first power, and (−) voltage and (+) voltage are respectively applied to the terminals $V_2$ and $V_4$ of second power, current applied to the odd-numbered segments 221A and 221C flows in a direction represented by the arrow $I_1$, and current applied to the even-numbered segments 221B and 221D flows in a direction represented by the arrow $I_2$. That is, the current $I_1$ and the current $I_2$ flow in opposite directions. As such, facing surfaces of each odd-numbered solenoid segment 221A or 221C and each even-numbered solenoid segment 221B or 221D have the same polarity, which results in generation of repulsive force between the respective solenoid segments 221A, 221B, 221C, and 221D.

Figure 6:
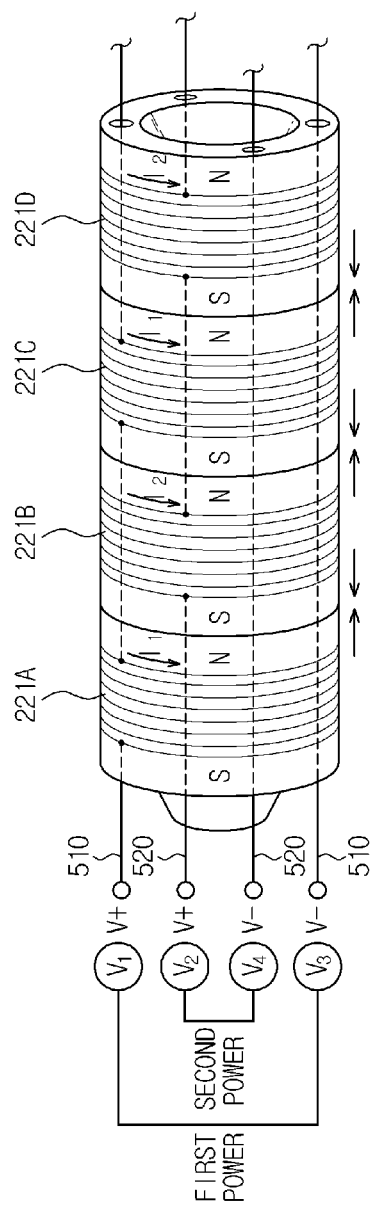
FIG. 6 is a view showing generation of attractive force between respective segments constituting the link of the surgical instrument of FIG. 4.

Referring to FIG. 6, if (+) voltage and (−) voltage are respectively applied to the terminals $V_1$ and $V_3$ of first power, and (+) voltage and (−) voltage are respectively applied to the terminals $V_2$ and $V_4$ of second power, current applied to the odd-numbered segments 221A and 221C flows in a direction represented by the arrow $I_1$, and current applied to the even-numbered segments 221B and 221D flows in a direction represented by the arrow $I_2$. That is, the current $I_1$ and the current $I_2$ flow in the same direction. As such, facing surfaces of each odd-numbered solenoid segment 221A or 221C and each even-numbered solenoid segment 221B or 221D have opposite polarities, which results in generation of attractive force between the respective solenoid segments 221A, 221B, 221C, and 221D.

That is, in a state in which all of the odd-numbered solenoid segments 221A and 221C are connected to the first coils 510 to receive first power and the even-numbered solenoid segments 221B and 221D are connected to the second coils 520 to receive second power, a current flow direction of first power and second power may be changed to be equal to or opposite to each other to cause change in the polarity of the respective solenoid segments 221A, 221B, 221C, and 221D, which results in generation of repulsive force or attractive force between the respective solenoid segments 221A, 221B, 221C, and 221D. In this case, the surgical instrument 220 may be in a bendable state under generation of repulsive force, and may be in a rigid state under generation of attractive force.

If repulsive force is generated between the respective solenoid segments 221A, 221B, 221C, and 221D, gaps are defined between the respective solenoid segments 221A, 221B, 221C, and 221D as exemplarily shown in FIG. 5. Thus, if external force $F_{ext}$ is applied to the link 221 as exemplarily shown in FIG. 7, the link 221 may bend in a direction in which the external force $F_{ext}$ is applied. As the link 221 of the surgical instrument 220 is configured to flexibly bend upon receiving the external force $F_{ext}$, the surgical instrument 220 may flexibly bend when to conform to the shape of the surgical instrument introduction passage (not shown) of the bent guide tube 240 when passing through the guide tube 240.

However, if the surgical instrument 220 remains bent during surgery after passing through the guide tube 240, the surgical instrument 220 may be difficult to manipulate and may be liable to cause dangerous situations. Therefore, during surgery, first power and second power may be applied such that current is applied to the respective solenoid segments 221A, 221B, 221C, and 221D in the same direction, which causes the surgical instrument 220 to be in a rigid state by attractive force between the respective solenoid segments 221A, 221B, 221C, and 221D.

To this end, the slave device 200 according to the present embodiment may include a first drive unit (not shown) to drive the respective solenoid segments 221A, 221B, 221C, and 221D. Here, the first drive unit may function to change the respective solenoid segments 221A, 221B, 221C, and 221D into electromagnets each having a specific polarity in response to a control signal transmitted from the master device 100.

For example, when attempting to insert the surgical instrument 220 into the guide tube 240 to prepare surgery as exemplarily shown in FIG. 3, the operator manipulates the input unit 110 of the master device 100 to switch the body 223 of the surgical instrument 220 into a bendable state to assist the surgical instrument 220 in easily passing through the bent guide tube 240. The controller (not shown) of the master device 100 generates a control signal corresponding to the state of the input unit 110 manipulated by the operator to transmit the control signal to the slave device 200. In this case, the generated control signal may be a signal to switch the body 223 of the surgical instrument 220 into a bendable state.

Thereafter, the slave device 200, which has received the control signal from the master device 100, may apply voltage, required to switch the body 223 of the surgical instrument 220 into a bendable state corresponding to the transmitted control signal, to the respective solenoid segments 221A, 221B, 221C, and 221D using the aforementioned first drive unit.

Meanwhile, when attempting to perform surgery on a defective region after the surgical instrument 220 completely passes through the guide tube 240, the operator manipulates the input unit 110 of the master device 110 to switch the body 223 of the surgical instrument 220 into a rigid state for convenience of surgery and enhancement of safety, and the controller (not shown) of the master device 100 generates a control signal corresponding to the state of the input unit 110 manipulated by the operator to transmit the control signal to the slave device 200. In this case, the generated control signal may be a signal to switch the body 223 of the surgical instrument 220 into a rigid state. Thereafter, the slave device 200 may apply voltage, required to switch the body 223 of the surgical instrument 220 into a state (rigid state) corresponding to the transmitted control signal, to the respective solenoid segments 221A, 221B, 221C, and 221D using the first drive unit.

In addition, the body 223 of the surgical instrument 220 according to the present embodiment may include a plurality of links 221 as exemplarily shown in FIG. 4 and a plurality of joints 227 to connect the links 221 to each other, without being in any way limited thereto. Here, the joints 227 may refer to movable joints and may have 1 DOF or more. The joints 227 may allow the body 223 to function as the wrist or the elbow, thereby assisting the operator in performing intuitive manipulation as if the operator were performing surgery by hand. To this end, the slave device 200 according to the present embodiment may include a drive unit (not shown) to drive each joint 227.

FIGS. 5 and 6 illustrate examples where solenoid segments 221A, 221B, 221C, and 221D are divided into odd-numbered solenoid segments 221A and 221C, which are connected to the first coils 510 to receive first power, and the even-numbered solenoid segments 221B and 221D, which are connected to the second coils 520 to receive second power. In this arrangement, solenoid segments 221A, 221B, 221C, and 221D are configured to generate a repulsive force between all segments (see FIG. 5) or to generate an attractive force between all segments (see FIG. 6). However, the disclosure is not limited thereto.

For example, solenoid segments 221A and 221B may be connected to the first coils 510 to receive first power, and solenoid segments 221C and 221D may be connected to the second coils 520 to receive second power. Accordingly, segments 221A and 221B may generate a mutual attractive force, and segments 221C and 221D may generate a mutual attractive force, while segments 221B and 221C may generate a mutual repulsive force. Therefore, the surgical instrument may generate additional bendable and rigid states in addition to those illustrated in FIGS. 5 and 6.

Furthermore, although the rigidity or flexibility of the solenoid segments is described as depending on the polarity of the first power compared to the second power, the disclosure is not limited thereto. For example, the rigidity or flexibility of the solenoid segments may also depend on the amount of power provided to the solenoid segments. A relatively high value first and second power may provide a higher rigidity or flexibility compared to a relatively low value first and second power. Accordingly, the rigidity of the solenoid segments may increase as the power increases, or vice versa, such that the solenoid segments have additional degrees of flexibility other than discrete rigid or bendable states.

Figure 7:
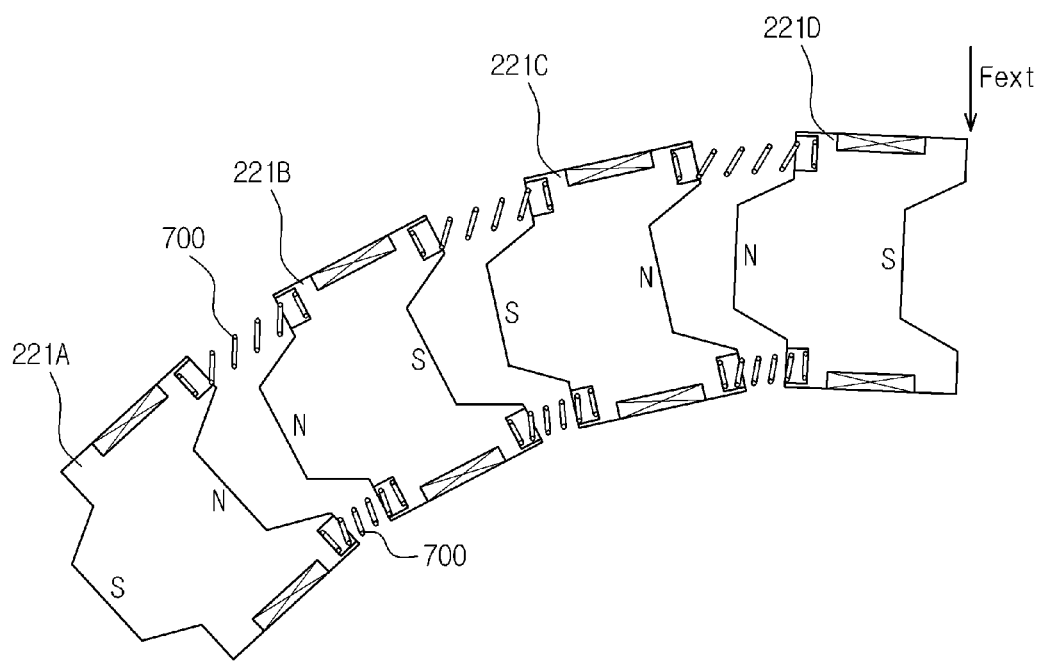
FIG. 7 is a view showing a configuration of the link that is deformable by external force when repulsive force is generated between the segments.

As exemplarily shown in FIG. 7, the surgical instrument 220 may further include elastic members 700 to connect the respective solenoid segments 221A, 221B, 221C, and 221D to one another. In this case, the elastic members 700 may be, for example, springs, without being in any way limited thereto. Provision of the elastic members 700 that connect the solenoid segments 221A, 221B, 221C, and 221D to one another may assist the solenoid segments 221A, 221B, 221C, and 221D in maintaining original arrangement thereof without unintentional separation even if a repulsive force is generated between the respective solenoid segments 221A, 221B, 221C, and 221D.

Figure 8:
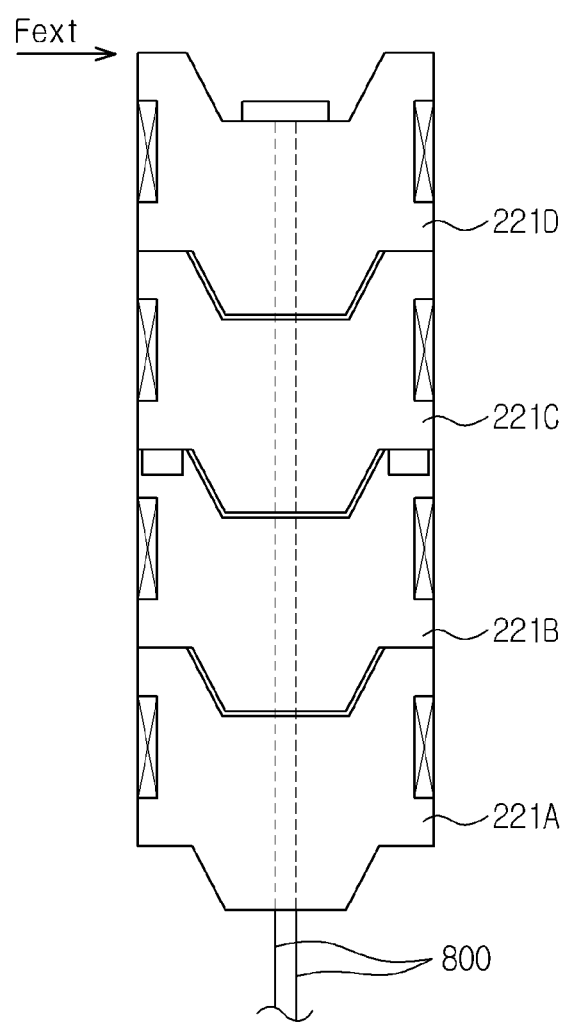
FIG. 8 is a view showing a wire penetrating the center of the respective solenoid segments.

Referring to FIG. 8, as described above, a variety of wires 800 having different functions may pass through the central passages of the respective solenoid segments 221A, 221B, 221C, and 221D. Here, the variety of wires 800 may include, for example, a wire to transmit drive power to the end effector 225 and a wire to enhance coupling strength between the solenoid segments 221A, 221B, 221C, and 221D when the solenoid segments 221A, 221B, 221C, and 221D are coupled to each other by attractive force, without being in any way limited thereto.

The end effector 225 is a part of the surgical instrument 220 that acts on a surgical region of the patient P. For example, the end effector 225 may include a clamp, grasper, scissors, staple applier, needle holder, scalpel, or cutting blade, for example, without being in any way limited thereto. Any other known instruments required for surgery may be used.

The body 223 of the surgical instrument 220 may have one end equipped with the end effector 225 and the other end mounted to an end of the robot arm 210. A second drive unit (not shown) to drive the end effector 225 may be provided at the end of the robot arm 210. In this case, the wire to transmit drive power to the end effector 225 may connect the end effector 225 and the second drive unit (not shown).

For example, to allow the end effector 225 to perform surgical motion, such as gripping, cutting, suturing, etc., on a defective region, the operator manipulates the input unit 110 of the master device 100, and the controller (not shown) of the master device 100 generates a control signal corresponding to the state of the manipulated input unit 110 to transmit the control signal to the slave device 200. Thereafter, the slave device 200 may drive the end effector 225 to perform surgical motion corresponding to the control signal transmitted from the master device 100 using the second drive unit (not shown). In this case, the wire 800 may serve to transmit drive power from the second drive unit (not shown) to the end effector 225.

The image capture unit 230 of the slave device 200 may include, for example, a stereo camera to acquire a 3D image and a lighting device, without being in any way limited thereto. In addition, in the present embodiment, the image capture unit 230 may be an endoscope, without being in any way limited thereto. Here, the endoscope may be selected from among various surgical endoscopes, such as a thoracoscope, arthroscope, rhinoscope, cystoscope, proctoscope, duodenoscope, and cardioscope, for example, in addition to a celioscope that is mainly used in robotic surgery. In addition, the slave device 200 may further include a drive unit (not shown) to drive the image capture unit 230.

Although the embodiments of the present disclosure have been shown and described, it would be appreciated by those skilled in the art that changes may be made in these embodiments without departing from the principles and spirit of the invention, the scope of which is defined in the claims and their equivalents.

What is claimed is:

1. A surgical robot comprising:
   a surgical instrument including,
      at least one link, the at least one link including a plurality of solenoid segments such that an adjacent pair of the plurality of solenoid segments are configured to one of repel and attract each other based on whether a direction of current flow is same or opposite in the adjacent pair of the plurality of solenoid segments; and
      an end effector on a distal end of the surgical instrument, the end effector including a surgical tool, the surgical tool configured to perform a minimally invasive surgical operation on a patient.

2. The surgical robot of claim 1, wherein the at least one link includes a first link and a second link, and the surgical instrument further comprises:
   a first joint configured to connect the first link to the second link.

3. The surgical robot of claim 1, wherein each of the plurality of solenoid segments are arranged in a straight line when the surgical instrument is in a rigid state.

4. The surgical robot according to claim 3, wherein, each of the plurality of solenoid segments includes a plurality of odd-numbered solenoid segments and a plurality of even-numbered solenoid segments, each of the plurality of odd-numbered solenoid segments are connected to a first coil, and each of the plurality of even-numbered solenoid segments are connected to a second coil.

5. The surgical robot of claim 4, wherein the first coil is configured to receive a first power and the second coil is configured to receive a second power.

6. The surgical robot of claim 5, wherein a first odd-numbered solenoid segment of the plurality of odd-numbered solenoid segments repels a first even-numbered solenoid segment of the plurality of even-numbered solenoid segments, if a direction of a first current flow of the first power is opposite a direction of a second current flow of the second power.

7. The surgical robot of claim 5, wherein a first odd-numbered solenoid segment of the plurality of odd-numbered solenoid segments is configured to attract a first even-numbered solenoid segment of the plurality of even-numbered solenoid segments, if direction of a first current flow of the first power is in same direction as direction of a second current flow of the second power.

8. The surgical robot of claim 1, wherein each of the plurality of solenoid segments define a central passage extending from a proximal end to a distal end of respective ones of the plurality of solenoid segments.

9. The surgical robot of claim 8, wherein the surgical instrument further comprises:
a coupling member configured to penetrate the central passage to enhance coupling strength between a first odd-numbered solenoid segment of the plurality of solenoid segments and a first even-numbered solenoid segment of the plurality of solenoid segments.

10. The surgical robot of claim 9, wherein the coupling member includes a wire.

11. The surgical robot of claim 1, further comprising:
a master device configured to control a slave device by transmitting a control signal thereto via a communication interface, the slave device including the surgical instrument.

12. The surgical robot of claim 11, wherein the slave device further comprises:
a first driver configured to drive the plurality of solenoid segments based on the control signal received from the master device.

13. The surgical robot of claim 12, wherein the slave device further comprises:
a second driver configured to operate the end effector based on the control signal received from the master device.

14. The surgical robot of claim 13, wherein the surgical instrument further comprises:
a wire configured to transmit drive power from the second driver to the end effector.

15. The surgical robot of claim 1, wherein the surgical instrument further comprises:
an elastic member connecting a first odd-numbered solenoid segment of the plurality of solenoid segments to a first even-numbered solenoid segment of the plurality of solenoid segments.

16. The surgical robot of claim 15, wherein the elastic member includes a spring.

17. The surgical robot of claim 1, further comprising:
a master device configured to,
generate a control signal based on an input received by a user of the master device, and
transmit the control signal to a slave device associated with the surgical instrument.

18. The surgical robot of claim 1, wherein
the at least one link has a first set of terminals and a second of terminals,
the first set of terminals configured to receive voltages having one of a same polarity and an opposite polarity, and
the second set of terminals configured to receive voltages having one of the same polarity and the opposite polarity.

19. The surgical robot of claim 18, wherein the at least one link is configured to selectively form a rigid straight line structure based on whether the first set of terminals and the second set of terminals receives voltages having the same polarity or the opposite polarity.

20. A robot comprising:
an instrument including at least one link, the at least one link including a plurality of solenoid segments, the plurality of solenoid segments including a plurality of odd-numbered solenoid segments and a plurality of even-numbered solenoid segments, the plurality of odd-numbered solenoid segments being connected to a first coil, and the plurality of even-numbered solenoid segments being connected to a second coil, such that adjacent ones of the plurality of odd-numbered solenoid segments and the plurality of even-numbered solenoid segments are configured to one of repel and attract each other based on whether a direction of current flow is same or opposite in the adjacent ones of the plurality of odd-numbered solenoid segments and the plurality of even-numbered solenoid segments.

21. The robot of claim 20, wherein the robot is a surgical robot and the instrument is a surgical instrument configured to perform minimally invasive surgery,
the instrument is configured to operate in a bent state, if power is applied to the first coil and the second coil such that a first current flowing through the plurality of odd-numbered solenoid segments is in an opposite direction as a second current flowing through the plurality of even-numbered solenoid segments, and
the instrument is configured to operate in a rigid state, if the power is applied to the first coil and the second coil such that the first current is in a same direction as the second current.

* * * * *